United States Patent
Lee et al.

(10) Patent No.: US 8,362,303 B2
(45) Date of Patent: Jan. 29, 2013

(54) PROCESS FOR PRODUCING AROMATIC ALDEHYDE COMPOUND

(75) Inventors: Yu-Chin Lee, Taipei (TW); Hsien-Yu Chang, Chiayi (TW); Han-Hsu Chen, Taichung (TW); Yu-Sen Hou, Kaohsiung (TW); Rong-Yi Liao, New Taipei (TW)

(73) Assignee: UFC Corporation, Taipei (TW)

( * ) Notice: Subject to any disclaimer, the term of this patent is extended or adjusted under 35 U.S.C. 154(b) by 142 days.

(21) Appl. No.: 13/084,653

(22) Filed: Apr. 12, 2011

(65) Prior Publication Data

US 2012/0264981 A1    Oct. 18, 2012

(51) Int. Cl.
    *C07C 45/61* (2006.01)
(52) U.S. Cl. ...................................................... 568/433
(58) Field of Classification Search ................... 568/433
    See application file for complete search history.

(56) References Cited

PUBLICATIONS

Albert Sezerat, Revelation des phenols en chromatographie sur papier a l'aide du phenitrazeole, Bull. Soc. Chem. Fr., p. 1193-1198 (1961).

Stewart A. Forsyth, et al., Utilisation of inonic liquid solvents for the synthesis of Lily-of-the-Valley fragrance . . . Journal of Molecular Catalysis A: Chemical 231 (1-2), 61-66 (2005).

Joseph A. Virgilio, et al., A Versatile Method for the Conversion of Ketones to Aldehydes, Organic Preparations and Procedures International, 14 (1-2), p. 2-20, (1982).

Xia, Yan, et al., Conjugated Organic Electroluminescent Molecules Based on Bipyridyl: Synthesis and Optical Properties, Chinese Journal of Organic Chemistry, 27 (5), 674-677 (2007).

*Primary Examiner* — Sikarl Witherspoon
(74) *Attorney, Agent, or Firm* — Stuart D. Frenkel; Frenkel & Associates, P.C.

(57) ABSTRACT

A process for producing an aromatic aldehyde compound has steps of converting alkyl-substituted or non-substituted benzene into a compound of formula I by halomethylation, and allowing the compound of formula I and alkyl aldehyde to react in presence of phase transfer catalyst at a reaction temperature under alkaline condition to obtain the aromatic aldehyde compound.

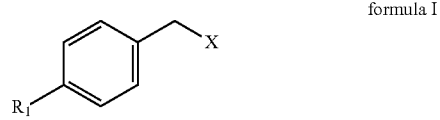

formula I

10 Claims, No Drawings

PROCESS FOR PRODUCING AROMATIC ALDEHYDE COMPOUND

BACKGROUND OF THE INVENTION

1. Field of the Invention

The present invention relates to a process for producing an aromatic aldehyde compound without hydrogen-reduction under high pressure and having advantages of low cost, high efficiency and low contamination.

2. Description of the Prior Arts

Synthetic aromatic compound is largely used in industries for producing perfumes or essence oils, which are useful for articles for daily use, such as soap, detergent, cosmetics and so on. Common synthetic aromatic compounds include aromatic aldehyde compounds, for example, lysmeral, floralozone and so on. Industrial production of aromatic aldehyde compounds is first developed by Givaudin Corporation. However, current techniques for industrial production of aromatic aldehyde compounds still have several problems.

A current process for producing an aromatic aldehyde compound is shown in Scheme I, wherein production of 4-tert-butyl-phenyl-formaldehyde is critical. The final step of the process requires hydrogen-reduction with palladium on carbon catalyst under high pressure. Use of noble metal as catalyst results in high cost of production. Patent NO. WO2007045641 owned by Badische Anilin- and Soda-Fabrik Corp. (BASF) aims at improving the final step for hydrogen-reduction of the above process. However, the reaction pressure is so high as 30 Bar, leading to difficulties in its industrialization.

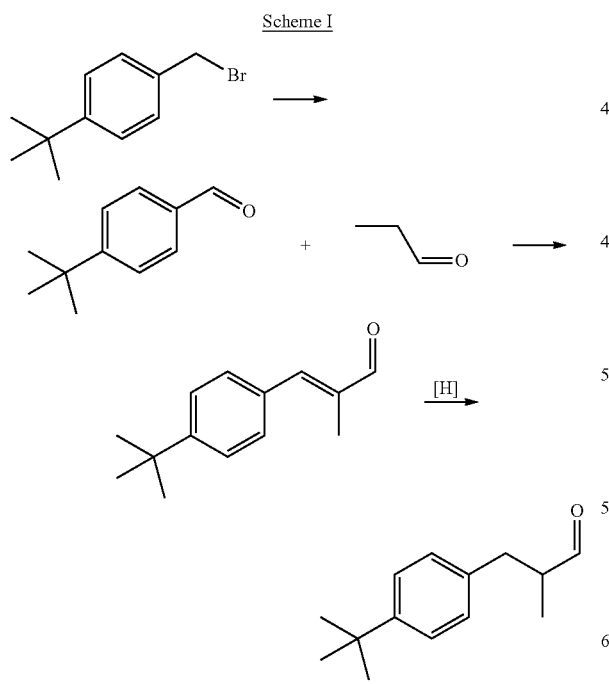

Givaudin Corporation discloses a process for producing an aromatic aldehyde in *Bull. Soc. Chem. Fr.*, p 1194 in 1961, as shown in Scheme II. The process utilizes great amounts of $TiCl_4$ and $BF_3\text{-}Et_2O$ as catalyst. However, it has a yield less than 10%. Moreover, one of the raw materials, 2-methylpropenal, is rare and difficult to be obtained, and $TiCl_4$ is easy to be hydrolyzed. Therefore, the process cannot be industrialized and will cause three wastes, that is, waste water, waste gas and industrial residue, leading to environmental pollutions.

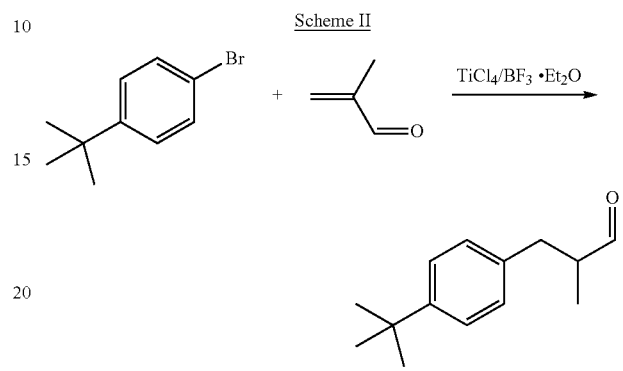

DE2627112 discloses a process for producing an aromatic aldehyde compound as shown in Scheme III. Although its yield is higher than 80%, one of the raw materials, 2-methylpropenal, is extremely rare and high-priced, resulting in the limitation of the process in industrial application. A process published in *Journal of Molecular Catalysis A: Chemical*, 231(1-2), 61-66 (2005) is a modification of the above process and achieves a theoretical production rate of 95%. However, the modified process requires use of 4-tert-butyliodobenzene as raw material, rare elements as catalyst, and ion liquid for reaction, and has a reaction time more than 24 hours, which leads to its low efficiency and failure in industrial application.

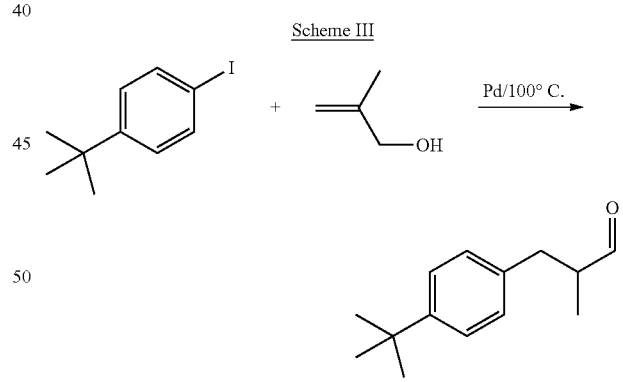

DE2851024 discloses a process for producing an aromatic aldehyde compound, as shown in Scheme IV. The process requires a great amount of $AlCl_3$, and has problems of three wastes and corrosion of manufacturing equipments. Furthermore, the known Vilsmeier reaction also has problems of three wastes and has a yield of only 35%. A process published in *Organic Preparations and Procedures International*, 14(1-2), p 2-20 is a modification of the above process. However, the modified process still requires hydrogen-reduction as a final step and utilizes noble metal as catalyst, contributing to its high production cost.

Scheme IV

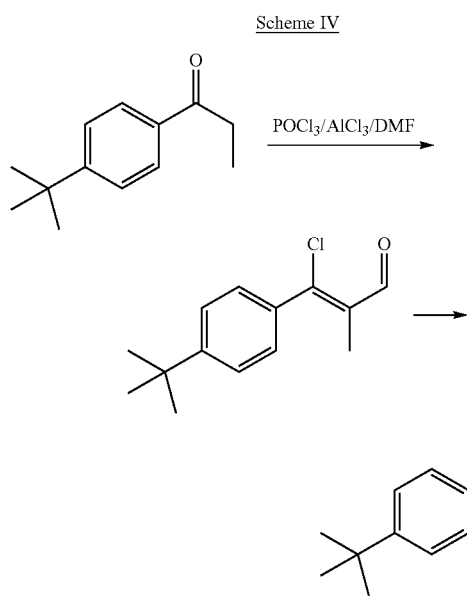

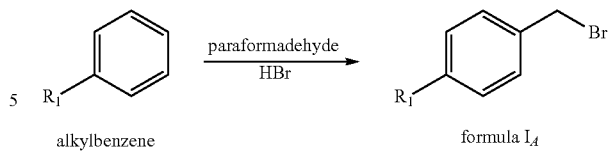

alkylbenzene     formula $I_4$

According to the present invention, said alkyl aldehyde is propanal or isopropanal.

According to the present invention, said alkaline condition is formed by addition of sodium hydroxide, potassium hydroxide or a combination thereof.

According to the present invention, said phase transfer catalyst is selected from the group consisting of:

(1) compound of formula II:

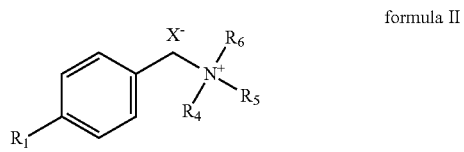

formula II wherein $R_1$ and X are defined as above; and $R_4$, $R_5$, $R_6$ are independently selected from alkyl groups having from 1 to 6 carbon atoms; and (2) tetraalkylammonium halide.

According to the present invention, said tetraalkylammonium halide can be, but not limited to, tetrabutylammonium iodide. According to the present invention, said reaction temperature preferably ranges from 60° C. to 90° C.; and more preferably, 70° C. to 80° C.

According to the present invention, said aromatic aldehyde compound is, but not limited to: lysmeral [i.e. 2-Methyl-3-(4-tert-butylphenyl)-propanal], floralozone [i.e. 3-(4-ethylphenyl)-2,2-dimethylpropanal], methyl lysmeral [i.e. 2,2-dimethyl-3-(3-methylphenyl)propanal], cyclamen aldehyde [i.e. 2-methyl-3-(p-isopropylphenyl)propanal], methyl cyclamen aldehyde [i.e. 2,2-dimethyl-4-(1-methylethyl)benzenepropanal] or 2,2-dimethyl-3-phenylpropanal.

The process in accordance with the present invention has advantages of: (1) using inexpensive and available compounds as raw material and catalyst, resulting in low cost; (2) being easy to operate; (3) causing none of the three waste problems and rare environmental pollution; (4) having high production yield over 60% and purity over 95%. Therefore, the process in accordance with the present invention is useful for large-scale industrial production.

Other objectives, advantages and novel features of the invention will become more apparent from the following detailed description when taken in conjunction with the accompanying drawings.

DETAILED DESCRIPTION OF THE PREFERRED EMBODIMENTS

As shown in scheme V, the process for producing an aromatic aldehyde compound according to the present invention comprises the steps of: subjecting alkyl-substituted or non-substituted benzene to halomethylation to form a compound of formula I; and allowing the compound of formula I and alkyl aldehyde to react in presence of phase transfer catalyst (PTC) at a reaction temperature under alkaline condition to obtain the aromatic aldehyde compound.

To overcome the shortcomings, the present invention provides a process for producing an aromatic aldehyde compound that requires no hydrogen-reduction under high pressure with expensive and complicated manufacturing equipments and will not cause pollution to environment to mitigate or obviate the aforementioned problems.

SUMMARY OF THE INVENTION

The present invention provides a process for producing an aromatic aldehyde compound. The process comprises steps of:

converting alkyl-substituted or non-substituted benzene into a compound of formula I by halomethylation, wherein $R_1$ is hydrogen, methyl, ethyl, isopropyl, isobutyl or tert-butyl group and X is halogen; and

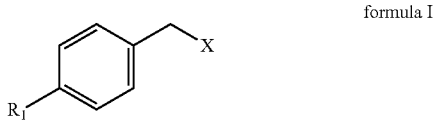

formula I allowing the compound of formula I and alky aldehyde to react in presence of phase transfer catalyst at a reaction temperature under alkaline condition to obtain the aromatic aldehyde compound.

According to the present invention, alkyl group in alkyl-substituted or non-substituted benzene is, for example, but not limited to: methyl, ethyl, isopropyl, isobutyl or tertbutyl.

According to the present invention, said halomethylation is performed by, for example, but not limited to: a method as described in *Youji Huaxue*, 27 (5), 674-677, 2007. Halomethylation suitable for the present invention, for example, has a common reaction including steps of: allowing an alkyl benzene and paraformaldehyde to react to form p-alkylphenol and then subjecting a substitution reaction with hydrogen halide, such as hydrogen bromide (HBr) to form the compound of formula $I_4$, wherein alkyl group ($R_1$) in the alkyl benzene is selected from the group consisting of hydrogen, methyl, ethyl, isopropyl, isobutyl and tertbutyl.

Scheme V

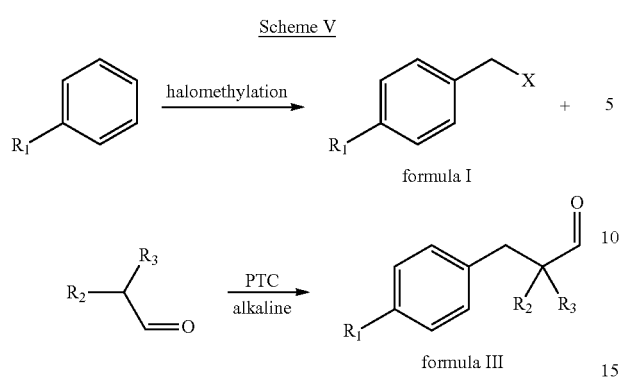

According to the present invention, $R_1$ is hydrogen, methyl, ethyl, isopropyl, isobutyl or tert-butyl group; $R_2$ is methyl or ethyl group; $R_3$ is hydrogen, methyl or ethyl group; and X is halogen group.

In an embodiment of the present invention, the phase transfer catalyst is tetraalkylammonium halide, wherein the alkyl group in tetraalkylammonium halide is $C_1$ to $C_6$ alkyl, for example, methyl, ethyl, isopropyl, isobutyl or tert-butyl group.

In an embodiment of the present invention, the reaction temperature ranges from 60° C. to 90° C.

In a preferred embodiment of the present invention, the reaction temperature ranges from 70° C. to 80° C.

EXAMPLES

The present invention was further illustrated by the following examples; it should be understood that the examples and embodiments described herein are for illustrative purposes only and should not be construed as limiting the embodiments set forth herein.

Example-1

Preparation of Compound 1

Compound 1 was obtained by Route 1 and experimental protocols as follows.

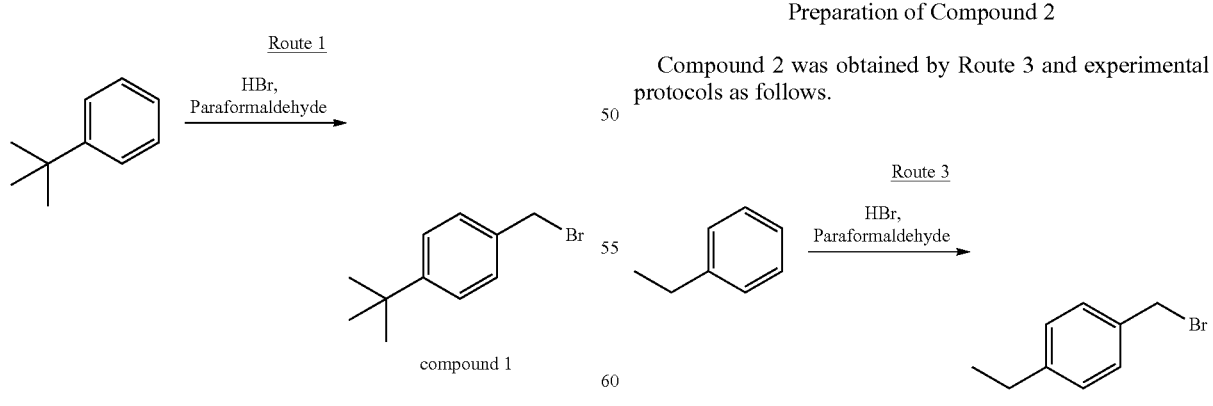

50 grams (0.37 mol) of tert-butylbenzene, 12.3 grams (0.40 mol) of paraformaldehyde and 100 mL of acetic acid were mixed in a flask. 109.6 grams of hydrogen bromide (HBr) in 33% (w/w) acetic acid solution was slowly added into the flask dropwise within 30 minutes and then heated to 120° C. and stirred for 7.5 hours. Samples were obtained and extracted with water and dichloromethane. Organic phase was obtained and subjected to thin-layer chromatography (TLC) for tracing reaction. Until reactants were consumed, 200 mL of water was added into the reaction mixture and then extracted with 200 mL dichloromethane for three times. Organic phases were collected, concentrated and distilled under a condition of a temperature of 165~170° C. and a pressure of $4.8~5.5\times10^{-1}$ torr to obtain distilled fractions. 73.02 grams of compound 1 was obtained with a yield of 86.3%.

Example-2

Preparation of Phase Transfer Catalyst 1 (PTC 1)

Phase transfer catalyst 1 (PTC 1) was obtained by Route 2 and experimental protocols as follows.

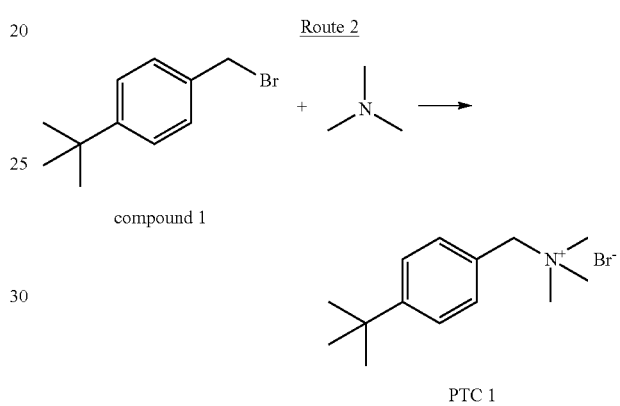

10 grams (220.1 mmol) of compound 1 was dissolved in 200 mL of anhydrous ethanol, followed by adding 14.31 grams (242.1 mmol) of trimethylamine, refluxing for 2 hours and standing overnight. Precipitate was obtained by filtration and rinsed with anhydrous ethanol for three times to obtain a solid, which was dried and ready for use as PTC 1 in the following examples.

Example-3

Preparation of Compound 2

Compound 2 was obtained by Route 3 and experimental protocols as follows.

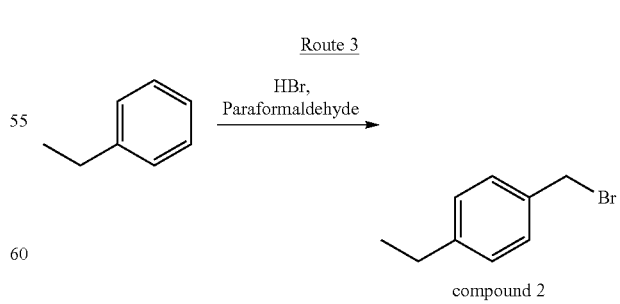

50 grams (0.47 mol) of ethylbenzene, 15.56 grams (0.52 mol) of paraformaldehyde and 100 mL acetic acid were mixed in a flask. 138.6 grams of hydrogen bromide in 33% (w/w) acetic acid solution was slowly added into the flask dropwise within 30 minutes and then heated to 120° C. and stirred for 7.5 hours. Samples were obtained and extracted with water and dichloromethane. Organic phase was obtained and subjected to TLC for tracing reaction. When the reaction was finished, 200 mL of water was added and extracted with 200 mL dichloromethane for three times. Organic phases were collected, concentrated and distilled under a condition of a temperature of 151~156□ and a pressure of 4.2~4.8× $10^{-1}$ torr to obtain distilled fractions. 81.66 grams of compound 2 was obtained with a yield of 86.9%.

Example-4

Preparation of Phase Transfer Catalyst 2 (PTC 2)

Phase transfer catalyst 1 (PTC 2) was obtained by Route 4 and experimental protocols as follows.

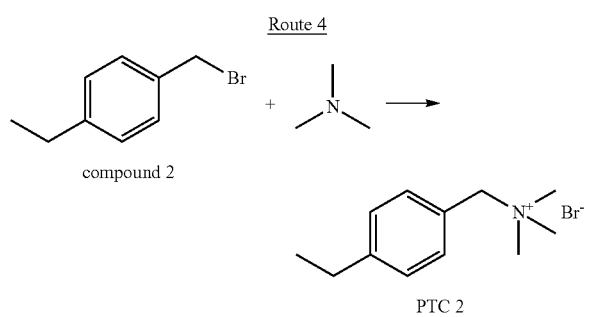

10 grams (251.2 mmol) of compound 2 was dissolved in 200 mL of anhydrous ethanol, followed by adding 16.33 grams (276.3 mmol) of trimethylamine, refluxing for 2 hours and standing overnight. Precipitate was obtained by filtration and rinsed with anhydrous ethanol for three times to obtain a solid, which was dried and ready for use as PTC 2 in the following examples.

Comparative Example-1

The present example was performed by the following experimental protocols to produce lysmeral.

2.3 grams (57.7 mmol) of sodium hydroxide, 0.33 grams (0.88 mmol) of tetrabutylammonium iodide, 7.5 mL water, 4.2 mL toluene, 1 mL tetrahydrofuran (THF) were mixed in a flask and then heated to 70~75° C. Mixture of 10 grams (44.0 mmol) of compound 1 and 3.55 grams (61.2 mmol) of propanal was slowly added into the flask dropwise within 2 hours while the reaction mixture was vigorously stirred. When addition was finished, the reaction mixture was stirred at 70-75° C. for 3 hours and traced by gas chromatography (GC). Until reactants were consumed, 30 mL water was added for extraction to obtain an organic phase. The organic phase was dehydrated with anhydrous sodium sulfate, filtered and concentrated by vacuum distillation. 4.84 grams of lysmeral was obtained with a yield of 53.8%.

Example-5

Preparation of Lysmeral

The present invention was performed according to the following Route 5 and experimental protocols to obtain lysmeral.

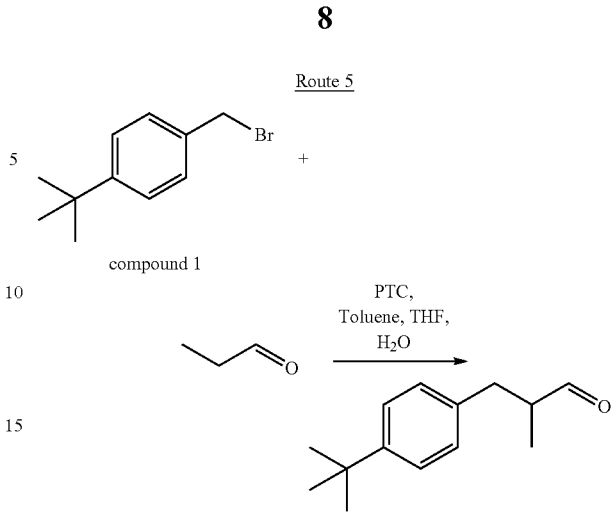

2.3 grams (57.7 mmol) of sodium hydroxide, 0.26 grams (0.88 mmol) of PTC 1, 7.5 mL of water, 4.2 mL of toluene, 1 mL of THF were mixed in a flask and then heated to 70-75° C. Mixture of 10 grams (44.0 mmol) of compound 1 and 3.55 grams (61.2 mmol) of propanal was added into the flask dropwise within 2 hours while the reaction mixture was vigorously stirred. While addition was finished, the reaction mixture was stirred at 70-75° C. for 3 hours and traced by GC. When the reaction stopped, 30 mL water was added for extraction to obtain an organic phase. The organic phase was dehydrated with anhydrous sodium sulfate, filtered and concentrated by vacuum distillation. 7.43 grams of lysmeral was obtained with a yield of 82.6% and verified to have a purity of 97.27% by GC analysis.

Results of analysis by NMR are shown as follows:

$^1$H NMR (CDCl$_3$) □δ 9.73 (t, 1H, J=6.851), 7.34 (ddd, 1H, J=8.032, J=3.716, J=0.000), 7.13 (ddd, 1H, J=8.032, J=3.732, J=0.000), 7.11 (ddd, 1H, J=8.032, J=3.716, J=0.000), 7.32 (ddd, 1H, J=8.032, J=3.732, J=0.000), 2.6 (dd, 2H, J=6.945, J=6.851), 3.0 (tq, 1H, J=6.945, J=6.911), 1.32 (m, 9H), 1.1 (d, 3H, J=6.911).

Results of Comparative Example-1 and Example-5 were shown in Table 1, demonstrating the yields of lysmeral were affected by catalyst and temperature. Table 1 illustrated that reactions with PTC 1 had higher yields than those with tetrabutylammonium iodide.

TABLE 1

| reaction temperature | phase transfer catalyst□ | yield |
|---|---|---|
| 20~25° C. | tetrabutylammonium iodide | no reaction |
|  | PTC 1 | no reaction |
| 50~60° C. | tetrabutylammonium iodide | 50.9% |
|  | PTC 1 | 63.1% |
| 70~75° C. | tetrabutylammonium iodide | 53.8% |
|  | PTC 1 | 82.6% |

□0.02 equivalent of phase transfer catalyst was used herein.

Comparative Example-2

The present example was performed by the following experimental protocols to produce floralozone.

2.63 grams (65.8 mmol) of sodium hydroxide, 0.37 grams (1.0 mmol) of tetrabutylammonium iodide, 7.5 mL of water, 4.2 mL of toluene, 1 mL of THF were mixed in a flask and then heated to 70~75° C. Mixture of 10 grams (50.2 mmol) of compound 2 and 5.03 grams (69.8 mmol) of isopropanol was added into the flask dropwise while the reaction mixture was vigorously stirred. When addition was finished, the reaction mixture was stirred at 70-75° C. for 3 hours and traced by GC. When the reaction stopped, 30 mL water was added for extraction to obtain an organic phase. The organic phase was dehydrated with anhydrous sodium sulfate, filtered and concentrated by vacuum distillation. 5.17 grams of floralozone was obtained with a yield of 54.1%.

Example-6

Preparation of Floralozone

The present invention was performed according to the following Route 6 and experimental protocols to obtain floralozone.

Route 6

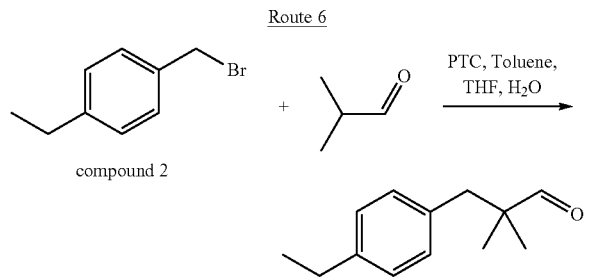

compound 2

2.63 grams (65.8 mmol) of sodium hydroxide, 0.27 grams (1.0 mmol) of PTC 2, 7.5 mL of water, 4.2 mL of toluene, 1 mL of THF were mixed in a flask and then heated to 70~75° C. Mixture of 10 grams (50.2 mmol) of compound 2 and 5.03 grams (69.8 mmol) of isopropanal was added into the flask dropwise while the reaction mixture was vigorously stirred. When addition was finished, the reaction mixture was stirred at 70-75° C. for 3 hours and traced by GC. When the reaction stopped, 30 mL of water was added for extraction to obtain an organic phase. The organic phase was dehydrated with anhydrous sodium sulfate, filtered and concentrated by vacuum distillation. 7.92 grams of floralozone was obtained with a yield of 82.8% and verified to have a purity of 95.76% by GC analysis.

Results of analysis by NMR are shown as follows:

$^1$H NMR (CDCl$_3$) □δ 9.62 (m, 1H), 7.15 (ddd, 4H, J=8.026, J=3.500, J=1.319), 2.8 (m, 2H), 2.6 (q, 2H, J=7.486), 1.2 (m, 9H).

Results of Comparative Example-2 and Example-6 were shown in Table 2, demonstrating the yields of floralozone were affected by catalyst and temperature. Table 2 illustrated that reactions with PTC 2 had higher yields than those with tetrabutylammonium iodide.

TABLE 2

| reaction temperature | phase transfer catalyst□ | yield |
| --- | --- | --- |
| 20~25° C. | tetrabutylammonium iodide | no reaction |
|  | PTC 2 | no reaction |
| 50~60° C. | tetrabutylammonium iodide | 51.7% |
|  | PTC 2 | 64.6% |
| 70~75° C. | tetrabutylammonium iodide | 54.1% |
|  | PTC 2 | 82.8% |

□0.02 equivalent of phase transfer catalyst was used herein.

Even though numerous characteristics and advantages of the present invention have been set forth in the foregoing description, together with details of the structure and features of the invention, the disclosure is illustrative only. Changes may be made in the details, especially in matters of shape, amount, and arrangement of parts within the principles of the invention to the full extent indicated by the broad general meaning of the terms in which the appended claims are expressed.

What is claimed is:

1. A process for producing an aromatic aldehyde compound, comprising:
converting alkyl-substituted or non-substituted benzene into a compound of formula I by halomethylation, wherein R$_1$ is hydrogen, methyl, ethyl, isopropyl, isobutyl or tert-butyl group and X is halogen; and

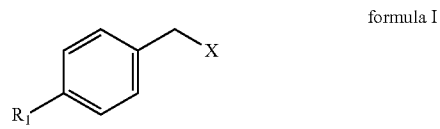

formula I allowing the compound of formula I and alky aldehyde to react in presence of phase transfer catalyst at a reaction temperature under alkaline condition to obtain the aromatic aldehyde compound.

2. The process of claim 1, wherein alkyl aldehyde is propanal or isopropanal.

3. The process of claim 1, wherein the phase transfer catalyst is selected from the group consisting of:
(1) compound of formula II:

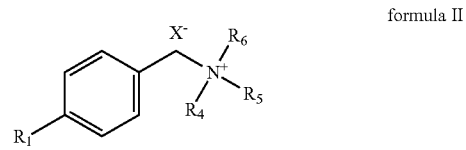

formula II wherein R$_4$, R$_5$, R$_6$ are independently selected from alkyl groups having from 1 to 6 carbon atoms;
(2) tetraalkylammonium halide.

4. The process of claim 1, wherein the reaction temperature ranges from 60° C. to 90° C.

5. The process of claim 2, wherein the reaction temperature ranges from 60° C. to 90° C.

6. The process of claim 3, wherein the reaction temperature ranges from 60° C. to 90° C.

7. The process of claim 1, wherein the reaction temperature ranges from 70° C. to 80° C.

8. The process of claim 2, wherein the reaction temperature ranges from 70° C. to 80° C.

9. The process of claim 3, wherein the reaction temperature ranges from 70° C. to 80° C.

10. The process of claim 1, wherein the aromatic compound is lysmeral, floralozone, 2,2-dimethyl-3-(3-methylphenyl)propanal, 2-methyl-3-(p-isopropylphenyl)propanal, dimethyl-4-(1-methylethyl)benzenepropanal or 2,2-dimethyl-3-phenylpropanal.

* * * * *